United States Patent [19]

Babiak et al.

[11] Patent Number: 5,252,763

[45] Date of Patent: Oct. 12, 1993

[54] PROCESS FOR PREPARING PROSTAGLANDIN ANALOGS

[75] Inventors: Kevin A. Babiak, Evanston; James R. Behling, Lindenhurst; John H. Dygos, Northbrook; John S. Ng, Chicago, all of Ill.

[73] Assignee: G. D. Searle & Co., Chicago, Ill.

[21] Appl. No.: 911,334

[22] Filed: Jul. 8, 1992

Related U.S. Application Data

[60] Continuation of Ser. No. 738,056, Jul. 30, 1991, abandoned, which is a division of Ser. No. 510,349, Apr. 17, 1990, Pat. No. 5,055,604.

[51] Int. Cl.$^5$ .......................... C07F 7/18; C07C 61/20
[52] U.S. Cl. ..................................... 556/110; 556/112
[58] Field of Search ................................ 556/110, 112

[56] References Cited

U.S. PATENT DOCUMENTS

| | | | |
|---|---|---|---|
| 3,932,479 | 1/1976 | Bernardy et al. | 260/448 |
| 3,950,406 | 4/1976 | Floyd et al. | 260/514 D |
| 3,962,351 | 6/1976 | Sih | 260/633 |
| 3,962,352 | 6/1976 | Sih | 260/633 |
| 3,962,353 | 6/1976 | Sih | 260/633 |
| 3,965,143 | 6/1976 | Collins et al. | 260/468 |
| 4,007,210 | 2/1977 | Bernardy et al. | 260/395 |
| 4,415,501 | 11/1983 | Grudzinskas et al. | 260/429 |
| 4,822,909 | 4/1989 | Arata et al. | 556/441 X |
| 4,904,820 | 2/1990 | Campbell et al. | 560/121 |
| 4,916,238 | 4/1990 | Cooper et al. | 549/214 |
| 4,983,753 | 1/1991 | Floyd | 560/121 X |

FOREIGN PATENT DOCUMENTS

| | | |
|---|---|---|
| 0153689 | 4/1985 | European Pat. Off. |
| 0178139 | 4/1986 | European Pat. Off. |
| WO91/15493 | 10/1991 | PCT Int'l Appl. |

OTHER PUBLICATIONS

Schwartz, Jeffrey, Transition Metal Hydride Reagents for Organic etc., J. Organomet. Chem. Library, 1, 461–488, Jan. 1976.

B. H. Lipshutz Applications of Higher-Order Mixed etc. Synthesis Reviews No. 4, 334,339 Apr. 1987.

K. F. Bernardy et al Prostaglandins and Congeners. 20. Synthesis of etc. The Journal of Organic Chemistry vol. 44, No. 9 1438–1447 Apr. 1979.

B. H. Lipshutz et al Hydrozirconation-Transmetalation. A Mild, etc. J. Am. Chem. Soc. vol. 112 7440–7441 Jan. 1990.

K. A. Babiak et al. One-Pot Synthesis of Protected Prostaglandins etc. J. Am. Chem. Soc. vol. 112 7741–7442 Jan. 1990.

M. J. Loots et al. Formaldehyde Trapping of Zirconium Enolates: etc. Tetrahedron Letters No. 45 4382 Jan. 1978.

*Primary Examiner*—Arthur C. Prescott
*Attorney, Agent, or Firm*—Roger A. Williams

[57] ABSTRACT

A process for preparing higher order cuprate complexes by reacting an alkyne with zirconocene chloride hydride to produce a zirconium intermediate which is reacted with an alkyllithium and a first copper reagent selected from R$^2$Cu(CN)Li or the mixture CuCN and R$^2$Li to produce a higher order cuprate complex.

4 Claims, No Drawings

PROCESS FOR PREPARING PROSTAGLANDIN ANALOGS

This is a continuation of application Ser. No. 07/738,056, filed Jul. 30, 1991, now abandoned, which is a divisional of application Ser. No. 510,349, filed Apr. 17, 1990, now U.S. Pat. No. 5,055,604.

BACKGROUND OF THE INVENTION

The invention herein is directed to a process for preparing prostaglandin analogs which can be performed in a single reaction vessel, in high yields and in the proper stereoconfiguration for the prostaglandin analogs. The invention herein is further directed to a process for preparing higher order cuprate complexes of the general formula

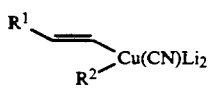

from alkenyl zirconium compounds as reactive intermediates in organic synthesis. The higher order cuprate complexes are derived from the reaction of a cuprate complex with an alkenyl zirconium compound. The higher order cuprate complexes are useful for preparing omega side chains of prostaglandin analogs and more specifically, 16-hydroxy prostaglandin analog side chains.

The state of the art of higher order cuprate complexes is summarized in *Synthesis*, 4, p. 325, (1987) where higher order cuprate complexes of the formulae $R_tRCu(CN)Li_2$, $R_tCu(2$-thienyl$)CNLi_2$, and $R_tRCU(SCN)Li_2$, uses are disclosed. $R_t$ represents the group transferred to an organic compound to form a carbon to carbon bond in a subsequent reaction with the disclosed higher order cuprate complex.

The use of zirconium compounds to prepare prostaglandins is shown in published European patent application 153,689 which describes the preparation of prostaglandin intermediates. The application describes a zirconium compound of the formula

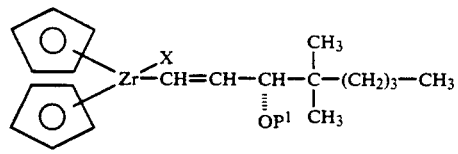

wherein X is a halogen and $P^1$ represents a hydrolyzable protecting group. The zirconium compound is reacted with a compound having the formula

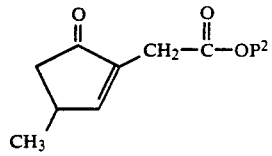

wherein $CO_2P^2$ represents a hydrolyzable ester group, in an anhydrous, inert organic solvent which contains a salt or a complex of a transition metal as a catalyst. The reaction mixture is treated with a protonating agent to produce a prostaglandin analog compound of the formula

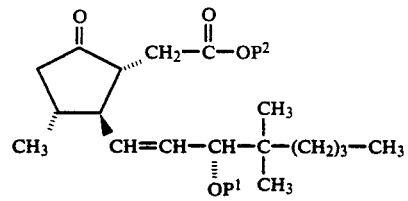

The reference describes the use of the zirconium compounds to add an unsaturated omega side chain on a cyclopentenone to form a prostaglandin analog. The reference discloses that the reaction occurs in the presence of a salt or a complex of a transition metal catalyst which includes salts or complexes of nickel, cobalt, iron, manganese and palladium. The reference's preferred complex is a complex or salt of nickel (I) which is produced in situ in the reaction by using a nickel (II) salt (or complex) and a reducing agent.

SUMMARY OF THE INVENTION

The present invention is directed to a process for preparing prostaglandin analogs (derivatives) using an organozirconium intermediate in reaction with a copper containing reagent to prepare a higher order cuprate complex. The higher order cuprate complex is reacted with a cyclopentenone to produce the prostaglandin derivative.

More particularly, the invention herein is directed to a process for preparing a higher order cuprate complex. The process is performed by reacting an alkyne of the formula

with zirconocene chloride hydride, $Cp_2Zr(H)Cl$, to produce an E-alkenyl zirconium intermediate of the formula

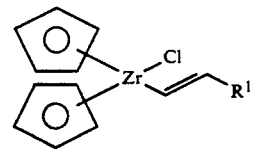

wherein $R^1$—CH=CH— is the omega side chain of a natural or synthetic prostaglandin and wherein any hydroxy group contained in the side chain is optimally protected by a suitable "hydrolyzable protective group." $R^1$ contains 1 to 20 carbon atoms which can have vinyl unsaturation. $R^1$ can contain cycloalkyl or cycloalkenyl moieties where the cycloalkyl contains 3 to 6 carbon atoms. $R^1$ can be substituted with hydroxy, tri-lower-alkylsiloxy, tetrahydropyranyloxy, tetrahydrofuranyloxy, halo or phenoxy.

The E-alkenyl zirconium intermediate is reacted with an alkyllithium and a copper-containing reagent selected from: $R^2Cu(CN)Li$ or the mixture CUCN and $R^2Li$ to produce a higher order cuprate complex intermediate of the formula

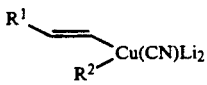

wherein $R^2$ can be alkyl, alkenyl, alkynyl, aryl or heteroaromatic such as 2-thienyl.

The above higher order cuprate intermediate can be reacted with a cyclopentenone of the formula

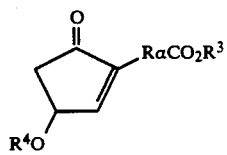

wherein $R_\alpha$ can be an alkyl, alkenyl, or alkynyl of 1 to 6 carbons and can contain heteroatoms such as sulfur or oxygen and $R^3$ can be hydrogen or a lower alkyl, $R^4$ represents a hydrolyzable protecting group, to produce a prostaglandin derivative having the general formula

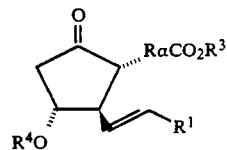

This invention herein further includes bringing into reactive contact an alkyne, zirconocene chloride hydride, a copper (I) salt such as copper cyanide, an alkyllithium or an alkynyllithium, and a suitable cyclopentenone of the formula

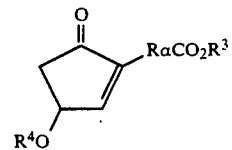

in a solvent such as THF, to produce a prostaglandin of the formula

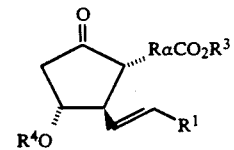

wherein the vinyl lower side chain in the produce was initially attached to zirconium.

DETAILED DESCRIPTION

The invention herein is directed to a process for preparing a higher order cuprate complex and prostaglandin derivatives from such a higher order cuprate complex. The process herein is advantageous in that the process can be performed in a single reaction vessel to completion either in forming the higher order cuprate complex or in forming the prostaglandin derivative in a stereospecific manner.

The invention herein is directed to a process for preparing prostaglandin derivatives by bringing into reactive contact an alkyne and a zirconium reagent of the formula, $Cp_2Zr(H)Cl$, to produce an E-alkenyl zirconium intermediate. The E-alkenyl zirconium intermediate is reacted with an alkyllithium and a copper-containing reagent which can be selected from: the complex $R^2Cu(CN)Li$ or the reactant mixture CUCN and $R^2Li$ to produce a higher order cuprate complex intermediate. The higher order cuprate complex intermediate can be reacted with an appropriately selected cyclopentenone to produce the desired prostaglandin derivative.

In a broader sense, the invention herein is directed to a method for preparing a higher order cuprate complex by the above mentioned process. The formed higher order cuprate complex can be used in further reaction sequences as is known for cuprate reagents for example to make prostaglandin derivatives.

The process is performed by reacting an alkyne and a zirconocene chloride hydride, $Cp_2Zr(H)Cl$, to produce an E-alkenyl zirconium intermediate. Cp represents a cyclopentadienyl anion group. The E-alkenyl zirconium intermediate need not be isolated but can be reacted with an alkyllithium and a copper-containing reagent which can be: the complex $R^2Cu(CN)Li$ or the reagent mixture CUCN and $R^2Li$ to produce a higher order cuprate complex intermediate of the formula

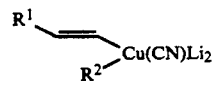

wherein $R^1$—CH=CH— is the omega side chain of a natural or synthetic prostaglandin and wherein any hydroxy group contained in the side chain is optimally protected by a suitable "hydrolyzable protective group." $R^1$ contains 1 to 20 carbon atoms which can have vinyl unsaturation. $R^1$ can contain cycloalkyl or cycloalkenyl moieties where the cycloalkyl contains 3 to 6 carbon atoms. $R^1$ can be substituted with hydroxy, tri-lower-alkylsiloxy, tetrahydropyranyloxy, tetrahydrofuranyloxy, halo or phenoxy; and wherein $R^2$ can be alkyl, alkenyl, alkynyl, aryl or heteroaromatic such as 2-thienyl.

The higher order cuprate complex intermediate need not be isolated but can be reacted with an appropriate cyclopentenone to produce a prostaglandin derivative of the formula

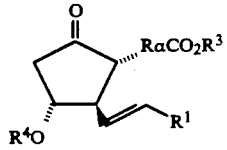

wherein $R_\alpha$ can be an alkyl, alkenyl, alkynl of 1 to 6 carbons. $R\alpha$ can contain heteroatoms such as sulfur or oxygen. $R^3$ can be hydrogen or a lower alkyl and $R^4$ represents a hydrolyzable protecting group. The expression "alkyl" used herein refers to straight chain and branched alkyl groups with 1 to 7 carbon atoms, such as methyl, ethyl, propyl and butyl. The expressions "halogen" or "halo" refer to halogen atoms such as fluorine, chlorine, bromine and iodine. The expression "aryl" refers to a mononuclear aromatic hydrocarbon group, such as phenyl, which can be unsubstituted or can be substituted in one or more positions by lower alkylenedioxy, halogen, nitro, lower alkyl or lower alkoxy groups; and polynuclear aryl groups, such as naphthyl, anthryl, phenanthryl and azulyl, which can be substituted by one or more of the groups mentioned above. The preferred aryl groups are substituted and unsubstituted mononuclear aryl groups, especially phenyl.

The expression "hydrolyzable protecting group" designates any protecting group which can be hydrolyzed with the formation of the group that it protects. Hydroxyl groups can be protected by forming hydrolyzable esters, acetals or ethers. Examples of groups that are suitable for forming esters to protect organic acids are lower alkyl groups or halo lower alkyl groups. A suitable ether protecting group can be a hydrolyzable lower alkyl ether, such as tertiary butyl ether and tetrahydropyranyl ether. Other ether groups are arylmethyl ethers, such as benzyl, benzhydryl or trityl ethers or α-lower-alkoxy-lower alkyl ethers, such as methoxymethyl ether, methoxypropyl ether or allyl ether, or tri-substituted silyl ethers in which the substituent is a lower alkyl and/or aryl group, such as trimethylsilyl ether, triethylsilyl ether or dimethyl tertiarybutylsilyl ether and dimethylphenylsilyl ether.

In the structural formulas herein, a wedge shaped bond ▼ represents a substituent which as the β orientation (above the plane of the molecule) and a line ≡ represents a substituent that is in the α orientation (below the plane of the molecule) and a wavy line ∼ represents a substituent which is either in the α or β orientation or is a mixture of these isomers.

The invention herein is illustrated in the following reaction Schemes I-II. The two reaction schemes illustrate the process herein and the variations in the process, any of which can be followed to produce a prostaglandin derivative. Each of the reaction sequences shown in the reaction schemes can be performed in a single reaction vessel which provides a particularly unique benefit for using the process herein as the performance of the process in a single reaction vessel ("one-pot" reaction) eliminates steps of separating and isolating intermediates and the need for having additional reaction vessels.

In the two reaction schemes an alkyne, which can contain additional unsaturation, is reacted with zirconocene chloride hydride to produce a zirconium intermediate which is reacted with an alkyllithium reagent, a copper complex (or reagents to produce the copper complex) and an enone ("enone" is used herein to refer to a cyclopentenone) to produce the prostaglandin derivative. In the reaction Schemes I-II, the processes described are exemplified with 4-methyl, 4-trimethylsilyloxy-1-octyne. It can be understood that other terminal alkynes, such as those described in examples 2-11, work equally well with the processes depicted in the Schemes I and II.

Scheme I

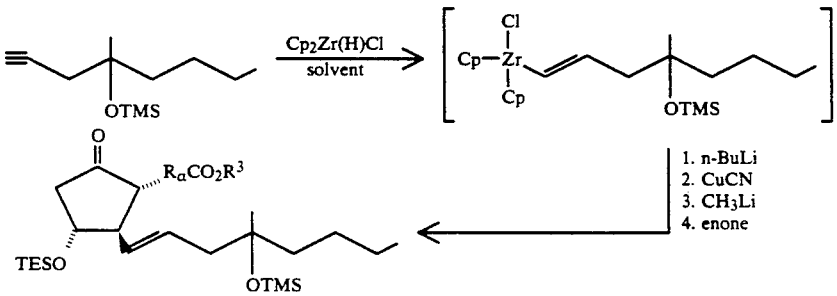

In the above reaction Scheme I a terminal alkyne is reacted with $Cp_2Zr(H)Cl$ in a suitable solvent such as tetrahydrofuran (THF) to produce a zirconium intermediate of the indicated formula. The zirconium intermediate is reacted sequentially with two equivalents of an alkyllithium such as n-butyllithium (n)BuLi) or methyllithium ($CH_3Li$), copper cyanide (CuCN), an alkyllithium such as methyllithium ($CH_3Li$) and an appropriate enone which results in the prostaglandin derivative which is represented in this Scheme I as having TMS and TES (trimethylsily and triethylsilyl) protective groups for the hydroxyl moieties on the prostaglandin derivative. The reaction is conducted in a single reaction vessel wit the reaction being added in the order indicated. The reaction is performed at a reduced temperature preferably in the range of −50° C. to −78° C.

Scheme II

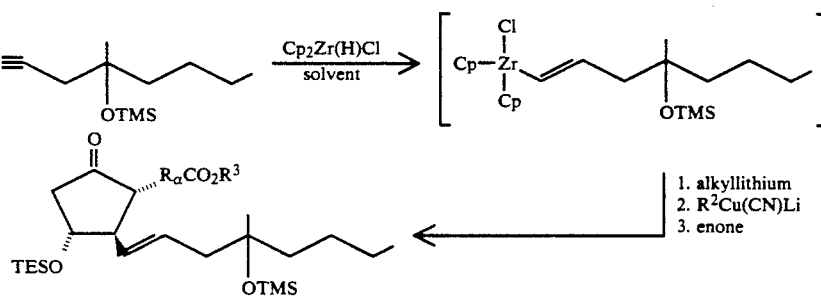

The reaction sequence shown in Scheme II illustrates another method for preparing prostaglandin derivatives using the invention herein. In reaction Scheme II a terminal alkyne is reacted with zirconocene chloride hydride to yield a zirconium intermediate which is reacted with two equivalents of alkyllithium followed by a lower order cuprate complex, $R^2Cu(CN)Li$, and a suitable enone to provide the prostaglandin derivative. The reaction sequence is performed in a temperature range from about $-50°$ C. to about $-78°$ C.

In the process herein any conventional inert organic solvent or solvent mixture can be used. Aromatic hydrocarbons such as benzene and toluene and ether solvents such as tetrahydrofuran are especially preferred. Temperatures in the range of $-50°$ to $-78°$ C. are preferred for performing the reaction with a temperature range from $-50°$ to $-60°$ C. being especially preferred.

EXAMPLE 1

(±)-Methyl (11α, 13E)-11,16-dihydroxy-16-methyl-9-oxoprost-13-en-1-oate

This example illustrates a one-pot preparation of a prostaglandin using the method herein and in particular following the reaction sequence shown in reaction Scheme I.

A dry, round bottom flask was charged with 776 mg (3.00 mmol) of zirconocene chloride hydride and 4 ml of dry THF under nitrogen. A solution of 604 mg (2.85 mmol) of 4-methyl-4-trimethylsilyloxy-1-octyne in 6 ml of THF was added by cannula. The mixture was stirred at room temperature for approximately 30 minutes and cooled to $-50°$ C. The mixture was treated with 3.56 ml of n-butyl-lithium (1.6M in hexane, 5.7 mmol) for ten minutes. To the vessel was added 254 mg (2.84 mmol) of copper cyanide and the mixture was stirred for fifteen minutes at $-50°$ C. followed by the addition of 2.09 ml of methyllithium (1.39M in cumene/THF, 2.9 mmol). The mixture was stirred for fifteen minutes to generate an orange cuprate solution. A solution of 503 mg (1.42 mmol) of (±)-methyl 7-1(3-triethylsilyloxy)-5-oxocyclopenten-1-yl]heptanoate in 4 ml of THF was added. After stirring for thirty minutes the product was poured onto a mixture of 25 ml of saturated aqueous ammonium chloride/ammonium hydroxide (9:1) and 50 ml ether. The quenched mixture was stirred for thirty minutes at room temperature, passed through a pad of Celite and separated. The Celite pad was washed successively with saturated annonium chloride and ether. The aqueous layer was extracted twice with 25 ml portions of ether. The combined organic layers were washed with saturated ammonium chloride/ammonium hydroxide (9:1), dried over anhydrous $Na_2SO_4$ and filtered through a pad of silica gel. The solvent was removed under vacuum to give the protected prostaglandin as a pale yellow oil. Deprotection was carried out by stirring the protected prostaglandin in 25 ml of 20% aqueous acetone in the presence of a catalytic amount of pyridinium p-toluenesulfonate (PPTS) for 4 hours to give 383 mg (71%) of (±)-methyl (11α,13E)-11,16-dihydroxy-16-methyl-9-oxoprost-13-en-1-oate after isolation and purification by chromatography on silica gel (ethyl acetate/hexane, gradient elution).

EXAMPLES 2-11

The procedure of Example 1 was repeated in every essential detail with the exception that the indicated enones, alkynes, and corresponding products shown in the following Table 1 were prepared. In examples 2 through 11 the enones had the following structures and the Ph in the structures in the Table represents a phenyl group.

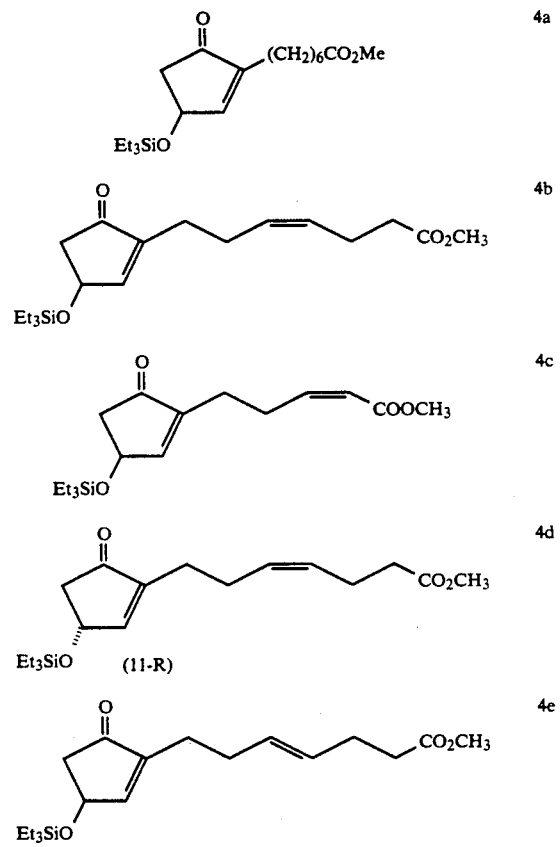

TABLE 1

| Example | Enone | Alkyne | Product | Yields |
|---|---|---|---|---|
| 2. | 4b | CH₃, OSiMe₃ (structure) | (structure) | >71% |

TABLE 1-continued

| Example | Enone | Alkyne | Product | Yields |
|---|---|---|---|---|
| 3. | 4b | (structure: HC≡C-CH₂-C(CH₃)(OSiMe₃)-CH=C(CH₃)₂) | (±) cyclopentanone product with Et₃SiO and OSiMe₃ groups, CO₂Me | >66% |
| 4. | 4b | (structure: HC≡C-CH₂-C(CH₃)(OSiMe₃)-CH₂-OPh) | (±) product with OPh, OSiMe₃, Et₃SiO, CO₂Me | >55% |
| 5. | 4b | (structure: HC≡C-CH₂-C(CH₃)(OSiEt₃)-CH=CH-C(CH₃)=CHEt) | (±) product with OSiEt₃, Et₃SiO, CO₂Me, Et | >80% |
| 6. | 4b | (structure: HC≡C-CH₂-C(CH₃)(OSiMe₃)-CH=CH-cyclopentenyl) | (±) product with OSiMe₃, Et₃SiO, CO₂Me, cyclopentenyl | 80% |
| 7. | 4b | (structure: HC≡C-CH₂-C(CH₃)(OSiEt₃)=cyclopentylidene) | (±) product with OSiEt₃, Et₃SiO, CO₂Me, cyclopentylidene | 61% |
| 8. | 4b | (structure: HC≡C-CH₂-C(CH₃)(OSiMe₃)-CH=CH-CH=C(CH₃)₂) | (±) product with OSiMe₃, Et₃SiO, CO₂Me | 73% |
| 9. | 4c | (structure: HC≡C-CH₂-C(CH₃)(OSiMe₃)-CH=CH-cyclopentenyl) | (±) product with OSiMe₃, Et₃SiO, CO₂Me, cyclopentenyl | 70% |
| 10. | 4d | (structure: HC≡C-CH₂-C(CH₃)(OSiMe₃)-CH=CH-cyclopentenyl) | (±) product with OSiMe₃, Et₃SiO, CO₂CH₃, cyclopentenyl | 70% |

TABLE 1-continued

| Example | Enone | Alkyne | Product | Yields |
|---|---|---|---|---|
| 11. | 4e | CH₃-alkyne with OSiMe₃ | (±) cyclopentanone product with COOCH₃, CH₃, OSiMe₃, Et₃SiO | >70% |

EXAMPLE 12

(±)-Methyl (11α, 13E)-11,16-dihydroxy-16-methyl-9-oxoprost-13-en-1-oate

This example illustrates the method herein employing reaction Scheme II to produce a prostaglandin derivative. To an argon filled, flame-dried flask was added 776 mg (7.0 mmol) of zirconocene chloride hydride under nitrogen. The flask was protected from light with foil. To this flask was added 4 ml of THF, followed by a solution of 604 mg (2.85 mmol) of 4-methyl-4-trimethylsilyloxy-l-octyne in 6 ml THF and 2 ml THF rinse. The reaction mixture was stirred at room temperature for approximately 30 minutes to give a light orange solution.

To a second flask was added 254 mg (2.85 mmol) of copper cyanide under nitrogen. To the cooled flask was added 5 ml THF and the reaction mixture was cooled to −78° C. To the flask was added via syringe 2.09 ml of methyllithium (1.39M in cumene/THF, 2.9 mmol). The flask was warmed to 0° C. for 12–20 minutes and recooled to −78° C. To the light orange colored solution of the zirconium intermediate at −78° C. was added n-butyllithium (3.56 ml, 5.7 mmol, 1.6M) dropwise by a syringe. The temperature was maintained at about −70° C. during the addition. The mixture was warmed gradually to −30° C. over fifteen minutes and held at −30° C. for fifteen minutes to give a deeper, orange-colored zirconium solution. The solution was recooled to −78° C. and the copper solution was added by cannula while maintaining the temperature at about −78° C. The reaction mixture was warmed briefly to −30° C. and recooled to −78° C. To the flask was added by syringe a solution of 503 mg (1.42 mmol) of (±)-methyl 7-[(3-triethylsilyloxy)-5-oxocyclopenten-1-yl]-heptanoate in 4 ml of THF. The reaction mixture was stirred at −78° C. for thirty minutes and quenched into 50 ml of a mixture of saturated aqueous ammonium chloride/ammonium hydroxide (9:1) and 50 ml of ether. The reaction mixture was stirred at room temperature for thirty minutes. The aqueous layer was extracted with two 50-ml portions of ether. The combined organic layers were washed twice with saturated ammonium chloride/ammonium hydroxide (9:1), and dried over anhydrous Na₂SO₄; filtered through Celite and concentrated at reduced pressure. The residue was dissolved in 50 ml of 4:1 acetone and water and treated with 50 mg PPTS and stirred at room temperature for four hours. The residue was partitioned between 20 ml saturated NaCl solution and 75 ml ethyl acetate. The aqueous phase was extracted with two 25-ml portions of ethyl acetate and the combined organic layers were washed with 10 ml saturated NaCl solution and dried over anhydrous Na₂SO₄. The solvent was removed in vacuo to yield 765 mg of crude (±)-methyl (11α, 13E)-11,16-dihydroxy-16-methyl-9-oxoprost-13-en-1-oate. The crude product was purified by column chromatography on silica gel to give 388 mg of purified product.

EXAMPLE 13

(±)-Methyl (11α,13E)-11,16-dihydroxy-16-methyl-9-oxoprost-13-en-1-oate

This example illustrates a one-pot preparation of a prostaglandin using the method herein and in particular following the reaction sequence shown in reaction Scheme I.

A dry, round bottom flask was charged with 776 mg (3.00 mmol) of zirconocene chloride hydride and 4 ml of dry THF under nitrogen. A solution of 604 mg (2.85 mmol) of 4-methyl-4-trimethylsilyloxy-l-octyne in 6 ml of THF was added by cannula. The mixture was stirred at room temperature for approximately 30 minutes and cooled to −50° C. The mixture was treated with 6.27 ml of methyllithium (1.39M in cumene/THF, 8.7 mmol) for fifteen minutes. To the vessel was added 254 mg (2.84 mmol) of copper cyanide and the mixture was stirred for one hour at −50° C. to generate an orange cuprate solution. A solution of 503 mg (1.42 mmol) of (±)-methyl 7-[(3-triethylsilyloxy)-5-oxocyclopenten-1-yl]heptanoate in 4 ml of THF was added. After stirring for thirty minutes the product was poured onto a mixture of 25 ml of saturated aqueous ammonium chloride/ammonium hydroxide (9:1) and 50 ml ether. The quenched mixture was stirred for thirty minutes at room temperature, passed through a pad of Celite and separated. The Celite pad was washed successively with saturated ammonium chloride and ether. The aqueous layer was extracted twice with 25 ml portions of ether. The combined organic layers were washed with saturated ammonium chloride/ammonium hydroxide (9:1), dried over anhydrous Na₂SO₄ and filtered through a pad of silica gel. The solvent was removed under vacuum to give the protected prostaglandin as a pale yellow oil. Deprotection was carried out by stirring the protected prostaglandin in 25 ml of 20% aqueous acetone in the presence of a catalytic amount of pyridinium p-toluenesulfonate (PPTS) for 4 hours to give 679 mg of crude (±)-methyl (11α,13E)-11,16-dihydroxy-16-methyl-9-oxoprost-13-en-1-oate after isolation. Quantitative high performance liquid chromatography analysis indicated the crude product contained 305 mg (53%) of the desired product.

EXAMPLE 14

(±)-Methyl (11α,13E)-11,16-dihydroxy-16-methyl-9-oxoprost-13-en-1-oate

This example illustrates a one-pot preparation of a prostaglandin using the method herein and in particular following the reaction sequence shown in reaction Scheme I.

A dry, round bottom flask was charged with 776 mg (3.00 mmol) of zirconocene chloride hydride and 4 ml of dry THF under nitrogen. A solution of 604 mg (2.85 mmol) of 4-methyl-4-trimethylsilyloxy-1-octyne in 6 ml of THF was added by cannula. The mixture was stirred at room temperature for approximately 30 minutes and cooled to −50° C. To the vessel was added 254 mg (2.84 mmol) of copper cyanide and the mixture was stirred for fifteen minutes at −50° C. followed by the addition of 6.27 ml of methyllithium (1.39M in cumene/THF, 8.7 mmol). The mixture was stirred for fifteen minutes to generate an orange cuprate solution. A solution of 503 mg (1.42 mmol) of (±)-methyl 7-[(3-triethylsilyloxy)-5-oxocyclopenten-1-yl]heptanoate in 4 ml of THF was added. After stirring for thirty minutes the product was poured onto a mixture of 25 ml of saturated aqueous ammonium chloride/ammonium hydroxide (9:1) and 50 ml ether. The quenched mixture was stirred for thirty minutes at room temperature, passed through a pad of Celite and separated. The Celite pad was washed successively with saturated ammonium chloride and ether. The aqueous layer was extracted twice with 25 ml portions of ether. The combined organic layers were washed with saturated ammonium chloride/ammonium hydroxide (9:1), dried over anhydrous $Na_2SO_4$ and filtered through a pad of silica gel. The solvent was removed under vacuum to give the protected prostaglandin as a pale yellow oil. Deprotection was carried out by stirring the protected prostaglandin in 25 ml of 20% aqueous acetone in the presence of a catalytic amount of pyridinium p-toluenesulfonate (PPTS) for 4 hours to give 383 mg (71%) of (±)-methyl (11α,13E)-11,16-dihydroxy-16-methyl-9-oxoprost-13-en-1-oate after isolation and purification by chromatography on silica gel (ethyl acetate/hexane, gradient elution).

EXAMPLE 15

(±)-Methyl (11α,4Z,13E)-11,16-dihydroxy-16-methyl-9-oxoprosta-4,13-dien-1-oate

This example illustrates a one-pot preparation of a prostaglandin using the method herein and in particular following the reaction sequence shown in reaction Scheme I.

A dry, round bottom flask was charged with 776 mg (3.00 mmol) of zirconocene chloride hydride and 4 ml of dry THF under argon. A solution of 604 mg (2.85 mmol) of 4-methyl-4-trimethylsilyloxy-1-octyne in 6 ml of THF was added by cannula. The mixture was stirred at room temperature for approximately 30 minutes and cooled to −50° C. To the vessel was added 254 mg (2.84 mmol) of copper cyanide and the mixture was stirred for fifteen minutes at −50° C. The mixture was treated with 6.27 ml (1.39 M in cumene, 8.71 mmol) of methyllithium via syringe and stirring was continued at −50° C. for fifteen minutes to generate a pale green solution. A solution of 501 mg (1.42 mmol) of (±)-methyl 7-[(3-triethylsilyloxy)-5-oxocyclopenten-1-yl] hept-4-en-1-oate in 4 ml of THF was added. After stirring for twenty minutes at −50° C., the product was poured onto a mixture of 25 ml of saturated aqueous ammonium chloride/ammonium hydroxide (9:1) and 50 ml ether. The quenched mixture was stirred for thirty minutes at room temperature and passed through a pad of Celite. The Celite pad was washed successively with saturated ammonium chloride and ether. The aqueous layer was extracted twice with 25 ml portions of ether. The combined organic layers were washed with saturated ammonium chloride/ammonium hydroxide (9:1), dried over anhydrous $Na_2SO_4$ and filtered through a pad of silica gel. The solvent was removed under vacuum to give the protected prostaglandin as a pale yellow oil. Deprotection was carried out by stirring the protected prostaglandin in 25 ml of 20% aqueous acetone in the presence of a catalytic amount of pyridinium p-toluenesulfonate (PPTS) for 4 hours to give 553 mg of crude deprotected prostaglandin. The contained yield of product was determined by HPLC quantitation of an aliquot of crude mixture versus a standardized curve of reference standard (4.6mm×25cm Zorbax Sil, 2 ml/min. 80/17/3 isooctane/dioxane/acetonitrile). In this manner, a 55% yield of (±)-methyl (11α,4Z,13E)-11,16-dihydroxy-16-methyl-9-oxoprosta-4, 13-dien-1-oate was obtained.

EXAMPLE 16

(±)-Methyl (11α, 4Z 13E)-11,16-dihydroxy-16-methyl-9-oxoprosta-4,13-dien-1-oate

A dry round bottom flask was charged with 776 mg (3.00 mmol) of zirconocene chloride hydride, 254 mg (2.85 mmol) of copper cyanide and 4 ml of dry tetrahydrofuran under argon. A solution of 604 mg (2.85 mmol) of 4-methyl-4-trimethylsilyloxy-1-octyne in 6 ml of THF was added by cannula. The mixture was stirred at room temperature for approximately 30 minutes and cooled to −50° C. The mixture was treated with 6.27 ml (1.39 M in cumene, 8.71 mmol) of methyllithium via syringe and stirring was continued at −50° C. for fifteen minutes to generate an olive-green solution. A solution of 501 mg (1.42 mmol) of (±)-methyl 7-[(3-triethylsilyloxy)-5-oxocyclopenten-1-yl]hept-4-en-1-oate in 4.0 ml of THF was added. After stirring for thirty minutes at −50° C., the product was poured onto a mixture of 25 ml of saturated aqueous ammonium chloride/ammonium hydroxide (9:1) and 50 ml ether. The quenched mixture was stirred for thirty minutes at room temperature and passed through a pad of Celite. The Celite pad was washed successively with saturated ammonium chloride and ether. The aqueous layer was extracted twice with 25 ml portions of ether. The combined organic layers were washed with saturated ammonium chloride/ammonium hydroxide (9:1),dried over anhydrous $Na_2SO_4$ and filtered through a pad of silica gel. The solvent was removed under vacuum to give the protected prostaglandin as a pale yellow oil. Deprotection was carried out by stirring the protected prostaglandin in 25 ml of 20% aqueous acetone in the presence of a catalytic amount of pyridinium p-toluenesulfonate (PPTS) for 4 hours to give 682 mg of crude deprotected prostaglandin. The contained yield of product was determined by HPLC quantitation of an aliquot of this sample versus a standardized curve of reference standard (4.6 mm×25 cm Zorbax Sil, 2 ml/min 80/17/3 isooctane/dioxane/acetonitrile). In this manner, a 35% yield of (±)-methyl (11α,4Z,13E)-11,16-dihydroxy-16-methyl-9-oxoprosta-4,13-dien-1-oate was obtained.

We claim:

1. A process for preparing a higher order cuprate complex comprising:
   reacting an alkyne with zirconocene chloride hydride to produce an E-alkenyl zirconium intermediate;

reacting the E-alkenyl zirconium intermediate with an alkyllithium and a lower order cuprate reagent selected from $R^2Cu(CN)Li$ or the mixture CUCN and $R^2Li$ to produce a higher order cuprate complex.

2. A process as recited in claim 1 wherein the reaction is performed in a temperature range from $-50°$ C. to $-78°$ C.

3. A process as recited in claim 1 wherein the lower order copper reagent comprises $R^2CU(CN)Li$.

4. A process as recited in claim 1 wherein the lower order copper reagent comprises the mixture CuCN and $R^2Li$.

* * * * *

UNITED STATES PATENT AND TRADEMARK OFFICE
CERTIFICATE OF CORRECTION

PATENT NO. : 5,252,763
DATED : October 12, 1993
INVENTOR(S) : Babiak, et al.

It is certified that error appears in the above-indentified patent and that said Letters Patent is hereby corrected as shown below:

Column 1, line 36, reading "$R_tRCU$" should read -- $R_tRCu$ --.

Column 1, line 36, reading "uses are" should read -- and their uses are --.

Column 2, line 59, reading "moities" should read -- moieties --.

Column 2, line 66, reading "CUCN" should read -- CuCN --.

Column 3, line 54, reading "the produce" should read -- the product --.

Column 4, line 5, reading "CUCN" should read -- CuCN --.

Column 4, line 24, reading "CUCN" should read -- CuCN --.

Column 4, line 56, reading "alkynl" should read -- alkynyl --.

Column 5, line 38, reading "which as the" should read -- which has the --.

Column 5, line 39, reading "and a line" should read -- and a broken line --.

Column 6, line 35, reading "(n)BuLi)" should read -- (n-BuLi) --.

Column 6, line 40, reading "(trimethylsily" should read -- (trimethylsilyl --.

UNITED STATES PATENT AND TRADEMARK OFFICE
CERTIFICATE OF CORRECTION

PATENT NO. : 5,252,763

DATED : October 12, 1993

INVENTOR(S) : Babiak, et al.

It is certified that error appears in the above-indentified patent and that said Letters Patent is hereby corrected as shown below:

Column 6, line 43, reading "wit the reaction" should read -- with the reactants --.

Column 7, line 37, reading "7-1(3-" should read -- 7-[(3- --.

Column 7, line 45, reading "annonium" should read -- ammonium --.

Column 15, line 4, reading "CUCN" should read -- CuCN --.

Column 16, line 4, reading "R²CU" should read -- R$^2$Cu --.

Signed and Sealed this

Seventeenth Day of January, 1995

*Attest:*

BRUCE LEHMAN

*Attesting Officer*    *Commissioner of Patents and Trademarks*